US005091495A

United States Patent [19]

Roux et al.

[11] Patent Number: 5,091,495

[45] Date of Patent: Feb. 25, 1992

[54] THEREOF AS POLYOLS IN THE FORMATION OF POLYURETHANES, POLYURETHANES ETC.

[75] Inventors: Gabriel Roux, Meylan; Janine Rivero, Fontaine; Alessandro Gandini, Saint-Martin-D'Uriage, all of France

[73] Assignee: Centre Scientifique et Technique de Battment, Paris, France

[21] Appl. No.: 580,152

[22] Filed: Sep. 10, 1990

Related U.S. Application Data

[62] Division of Ser. No. 229,169, Aug. 22, 1988, Pat. No. 4,973,715.

[51] Int. Cl.[5] .............................................. C08G 18/30

[52] U.S. Cl. ........................................ 528/49; 528/73

[58] Field of Search .................................... 528/49, 73

[56] References Cited

U.S. PATENT DOCUMENTS 4,426,460 1/1984 Pentz .................................... 528/73

*Primary Examiner*—Maurice J. Welsh

*Attorney, Agent, or Firm*—Rosen, Dainow & Jacobs

[57] ABSTRACT

This invention relates to novel furan polyols, which are characterized in that they are the product of reaction of a strain selected from the group or consisting of a polyalcohol, a monoamine or polyamine, said polyalcohol or said amine possibly containing a furan cycle and mixtures thereof with a chain extension agent constituted by an organic epoxide, with the proviso that this organic epoxide is a furannic oxiran when this polyalcohol does not contain a furan cycle with the exclusion of 2,5(bis-hydroxy)furan as sole strain, when the chain extension agent does not contain any furan cycle. These furan polyols are used for the preparation of polyurethane foams having improved properties.

49 Claims, No Drawings

THEREOF AS POLYOLS IN THE FORMATION OF POLYURETHANES, POLYURETHANES ETC.

This is a division of application Ser. No. 07/229,169, filed Aug. 22, 1988 now U.S. Pat. No. 4,973,715.

The present invention essentially relates to novel furan polyols, to the use thereof as polyols in the formation of polyurethanes, to polyurethanes thus obtained, and to a process for preparing same.

The flame-retardant properties of the furan cycle owing to the self-extinguishing property of the charring which is formed when compounds containing a furan cycle are burnt, are already know, cf. U.S. Pat. No. 4,029,611, U.S. Pat. No. 3,865,757 and U.S. Pat. No. 4,318,999.

In particular, in U.S. Pat. No. 4,318,999, the furan compound is constituted by 2,5-bis-(hydroxymethyl)-furan in combination with a halogenated polyol to constitute the polyol component made to react with an isocyanate, for the manufacture of rigid polyurethanes with improved flame resistance. Comparisons are made with furfurylalcohol or with polyhydroxyfuran as the sole polyol ingredient (tests B and C, Table 1, columns 5 and 6).

Similarly, FR-A-2 536 750 describes novel furan compounds with terminal hydroxy groups, capable of forming active components of rigid compositions of urethane and of isocyanurate with reduced inflammability. The use of 2,5-bis-(hydroxymethyl) furan (BHMF) is described, of which the chain extension is obtained by propoxylation (page 4, lines 6-12, Examples 1, 2). The use is preferred of homopolymers of BHMF (page 4, line 13 to page 9, line 30; Example 3, BHMFP Table III, Example 5, Example 6, claims).

However, it has appeared that the BHMF presents a low reactivity, which considerably limits the use thereof.

Likewise, it has appeared that the mechanical properties of these polyurethanes were still unsatisfactory, particularly their dimensional stability in damp heat as well as an insufficient behaviour in temperature.

It is therefore an object of the present invention to solve the new technical problem consisting in providing a solution furnishing novel polyols of the furan type capable of significantly improving the behaviour of polyurethanes in temperature, their dimensional stability in damp heat.

The present invention makes it possible to solve this new technical problem for the first time in satisfactory manner.

According to the present invention, novel furan polyols are thus produced, characterized in that they are the product of reaction of:

a) a strain selected from the group consisting of a polyalcohol, a monoamine or polyamine, said polyol or said amine possible containing at least one furan cycle, and mixtures thereof:

b) with a chain extension agent, possibly containing at least one furan cycle constituted by an organic epoxide, with the proviso that this organic epoxide is a furannic oxiran when this strain does not contain a furan cycle; with the exclusion of 2,5-bis-(hydroxymethyl)furan as sole strain, when the chain extension agent does not contain a furan cycle.

According to a particular feature, this amine is a primary or a secondary (mono- or poly-)amine.

According to another feature, this amine can contain one or several hydroxy functions (groups). When this amine contains at least a hydroxy function, preferably at least two hydroxy functions, said hydroxylated amine can be a tertiary amine. This hydroxylated amine is simultaneously a polyalcohol of the invention which is aminated.

According to a preferred embodiment, the polyalcohol mentioned above responds to the following chemical formula (I).

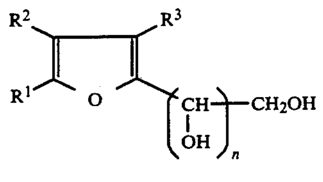

in which $R^1$, $R^2$, $R^3$ may be identical or different and represent H, a lower alkyl group with $C_1$-$C_5$, preferably $C_1$-$C_3$, an aliphatic group with alcohol function with $C_1$-$C_4$, an aliphatic group with acid function with $C_1$-$C_4$ or ester with a lower alkyl ester radical with $C_1$-$C_5$, preferably $C_1$-$C_3$, an aliphatic group with ketone function with $C_1$-$C_4$, an aliphatic group with aldehyde function with $C_1$-$C_4$; n=0 to 10, with the proviso, that, when n=0, at least one of the $R^1$, $R^2$, $R^3$ is a group with alcohol function, $R^1$ not being able to be —$CH_2OH$ if the chain extension agent does not contain a furan cycle; preferably n=1 to 10, and, further preferably n=1 to 3.

The aliphatic groups hereinabove are preferably straight-chain but may be branched.

According to another preferred feature, $R^1$ is selected among —H, —$CH_2OH$ with, in that case, n=1 to 10, or —$CH_3$.

According to another preferred feature, $R_2$ is selected from

—H, 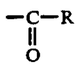

or —COOR with R=H or a lower alkyl group with $C_1$-$C_5$, preferably $C_1$-$C_3$, and preferably still —$CH_3$ or —$C_2H_5$.

According to a particular embodiment, the polyalcohol mentioned above is a furannic polyalcohol corresponding to the following formula:

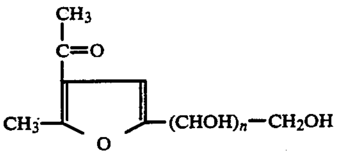

with n=1 to 10, preferably 1 to 3.

According to another variant, the starting polyalcohol is an aliphatic polyalcohol with $C_1$-$C_4$, preferably selected from ethylene-glycol, propylene-glycol, glycerine, trimethylolpropane, pentaerythritol, sorbitol.

According to another variant, said (mono- or poly-) amine can contain one or several hydroxy functions, thereby constituting an aminated polyalcohol which can be advantageously obtained by reacting a primary or secondary(mono- or poly-) amine with a chain extension agent constituted by the herein defined organic epoxide which can be a furannic epoxide.

According to a particular feature, it can be cited without limitation, as said starting invention amine; $NH_3$, methylamine, methylenediamine, ethylamine, ethylenediamine, propylamine, 1,3-propyldiamine, EDTA, as well as the corresponding mono- or polyhydroxylated amines. A preferred example of hydroxylated amine, or of aminated polyalcohol used as strain is triethanolamine.

According to yet another particular feature of the invention, the organic epoxide mentioned above is constituted by propylene oxide.

According to another embodiment of the invention, the organic epoxide mentioned above is constituted by a furannic oxiran of formula (II):

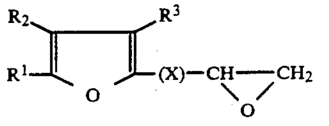

(II)

with $R^1$, $R^2$, $R^3$ having the same significance as for the polyalcohol of formula (I) mentioned above.

And (X) represents either a single carbon-carbon bond or an organic radical, preferably an aliphatic radical, advantageously having from 1 to 10 atoms of carbon.

According to another feature of the invention, it also covers the use of the above-mentioned furan polyols for constituting a part of all of the polyols employed in the formation of polyurethanes including polyisocyanurates by reaction in particular with isocyanates.

The present invention also covers the polyurethanes, including polyisocyanurates, characterized in that they are obtained by reaction of isocyanates with polyols of which at least part is constituted by furan polyols, such as defined hereinabove. The invention also covers the process for preparing these furan polyols as defined in the claims.

It has thus been observed that the novel furan polyols according to the invention make it possible, in completely unexpected manner, to improve the behaviour of the polyurethanes in temperature, their dimensional stability in damp heat.

The improvement of the properties naturally depends on the proportion of these furan polyols according to the invention in the mixture used for preparing the polyurethanes. It is preferred that the furan polyols according to the invention be the only polyols used in the reaction, although it is possible to use them in combination with other polyols.

The proportion of the incorporation of the polyols according to the invention may be modified to broad limits. However, it is preferred to respect a number of NCO/number of OH ratio higher than or equal to 1 so as to have an NCO number in excess with respect to the OH number, in particular to form polyisocyanurates.

All types of polyurethanes or polyisocyanurates, supple or rigid, expanded or not, may naturally be produced with the polyols according to the invention, whatever their process of production.

Other objects, characteristics and advantages of the invention will appear clearly to the man skilled in the art from the following Examples given simply by way of illustration and in no way limiting the scope of the present invention.

EXAMPLE 1

The starting polyalcohol is constituted by acetyl-3-(D-arabinotetroxybutyl) 5l-methyl 2l-furan of following formula:

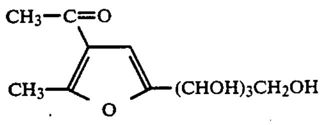

Reaction is effected with propylene oxide as chain extension agent, the proportion by weight of the propylene oxide relatively to the polyalcohol mentioned above being 57%, for 6 hours at a temperature of 150° C., using 250 ppm of KOH as catalyst.

A furan polyol is thus obtained, having a hydroxyl index equal to 610, determined by the conventional method, and indicating the number of OH functions/kg of polyol expressed by weight of KOH.

The functionality of this furan polyol is 4 and its viscosity expressed in centipoises at 20° C. is equal to about 50000.

This furan polyol is used for the preparation of polyurethane foams, bearing reference $F_1$, in accordance with the following formulation, after having neutralized KOH by tartric acid.

Formulation $F_1$:
Furan polyol hereinabove: 100 parts
Surfactant (Sr242 ® of Schell): 2 parts
Catalyst (DMACHA ® of BASF): 2 parts
Water: 1 part
Expanding agent (Freon ®): 40 parts
Isocyanate MDI: 170 parts The reaction is carried out in conventional manner and a cream time of 13 s is obtained, as well as a filament time of 67 s.

The characteristics of the foam are as follows:
Density ($kg/m^3$): 23 apparent in free expansion
$\lambda_o$(mW/m° C.): 0.023
$\lambda_\infty$ " ": 0.029
Temperature of the end of degradation of the urethanes (° C.): 320
Loss of weight (%): 26
ΔP %, 400° C. (%): 39

$\frac{\Delta V}{V}$ (%) (after 14 days at 70° C., 95% RH) (%): 2.4

EXAMPLE 2

The starting polyalcohol is constituted by 3-(D-arabino-tetroxybutyl) 5-methyl 2-furan ethyl acetate of following formula:

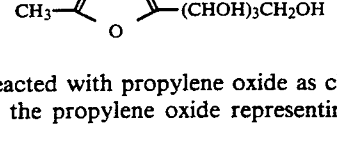

which is reacted with propylene oxide as chain extension agent, the propylene oxide representing 52% by weight of the above furan polyalcohol, for 20 hrs. at a temperature of 180° C., without catalyst.

A furan polyol is obtained having a hydroxyl index of 570, functionality of 4, a viscosity in centipoises at 20° C. equal to about 45000.

A formulation of polyurethane foam is made from this furan polyol according to the following formulation, referenced $F_2$:

Formulation $F_2$:
Polyol mentioned above: 100 parts
Surfactant (Sr242 ® of Schell): 2 parts
Catalyst (DMCHA ® of BASF): 2 parts
$H_2O$: 1 part
Expanding agent (Freon ®): 40 parts
Isocyanate MDI: 160 parts By mixing these components, a polyurethane foam is obtained which presents a cream time of 20 s and a filament time of 80 s.

The characteristics of this foam are as follows:
Density (kg/$m^3$)
apparent in free expansion: 21
$\lambda$o(mW/m° C.): 21
Temperature of the end of degradation of the urethanes (° C.): 340
Loss of weight (%): 33
Δ P %, 400° C. (%): 45

$\frac{\Delta V}{V}$ (%) (after 14 days at 70° C., 95% RH) (%): 2

EXAMPLE 3

The starting polyalcohol is constituted by 3-(D-arabino-tetroxyburyl) 5-methyl 2-furan methyl acetate of following formula:

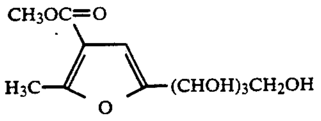

which is reacted with propylene oxide as chain extension agent, with a proportion of propylene oxide of 52% by weight, relatively to the above furan, for 9 hours at a temperature of 180° C., without catalyst.

A furan polyol is thus obtained having a hydroxyl index equal to 570, functionality of 4, and a viscosity in centipoises at 20° C. equal to about 45000.

This furan polyol thus obtained is then used for the formulation of polyurethane foam according to the following formulation referenced $F_3$:

Formulation $F_3$:
Furan polyol: 100 parts
Surfactant (Sr242 ® of Schell): 2 parts
Catalyst (DMCHA ® of BASF): 2 parts
$H_2O$: 1 part
Expanding agent (Freon ®): 40 parts
Isocyanate MDI: 160 parts With such a formulation, a cream time of 38 s is obtained and a filament time of 75 s, and the polyurethane foam obtained presents the following characteristics:
Density (kg/$m^3$) apparent in free expansion: 22
$\lambda$°mW/m° C.): 20
Temperature of the end of degradation of the urethanes (° C.): 320
Loss of weight (%): 38
ΔP %, 400° C. (%): 42.5

$\frac{\Delta V}{V}$ (%) (after 14 days at 70° C., 95% RH) (%): 3

EXAMPLE 4

The starting polyalcohol is constituted by 2,5-furfuryl dialcohol of following formula:

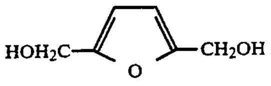

which is reacted with furyloxiran as chain extension agent, the proportion of furyloxiran being 64% by weight with respect to the above-mentioned furfuryl dialcohol, for 48 hours, at ambient temperature, without catalyst.

The furan polyol thus obtained presents a hydroxyl index of 250, a functionality of 2 and a viscosity in centipoises at 20° C. equal to about 20000.

This furan polyol thus obtained is used for the formulation of polyurethane foam, according to the following formulation referenced $F_4$:

Formulation $F_4$:
Furan polyol hereinabove: 100 parts
Surfactant (Sr242 ® of Schell): 2 parts
Catalyst (DMCHA ® of BASF): 2 parts
$H_2O$: 1 part
Expanding agent (Freon ®): 40 parts
Isocyanate MDI: 79 parts
Non-reactive fluidizing agent: 5 parts This formulation has an ultra-rapid speed of reaction which does not enable its cream time nor its filament time to be determined.

The characteristics of the polyurethane foam thus obtained are as follows:
Density (kg/$m^3$) apparent in free extension: 27
$\lambda$o(mW/m° C.): 21
Temperature of the end of degradation of the urethanes (° C.): 330
Loss of weight (%): 17
ΔP %, 400° C. (%): 42

$\frac{\Delta V}{V}$ (%) (after 14 days at 70° C., 95% RH) (%): 2

EXAMPLE 5

The starting polyalcohol is constituted by ethylene glycol as aliphatic polyalcohol of formula $CH_2OH—CH_2OH$ which is reacted with furyloxiran of following formula:

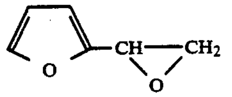

the proportion of furyloxiran being 72% by weight with respect to the ethylene glycol, for 24 hrs. and at 55° C., without catalyst.

The furan polyol thus obtained presents a hydroxide index equal to 500, a functionality of 2 and a viscosity in centipoises at 20° C. equal to about 20000.

The furan polyol thus obtained is used for a formulation of polyurethane foam referenced $F_5$, which is as follows:

Formulation $F_5$:
Furan polyol hereinabove: 100 parts
Surfactant (Sr242 ®) of Schell): 2 parts
Catalyst (DMCHA ® of BASF): 2 parts
$H_2O$: 1 part
Expanding agent (Freon ®): 40 parts
Isocyanate MDI: 142 parts By mixing these components, a polyurethane foam can be prepared, which presents a cream time of 15 s and a filament time of 20 s.

The characteristics of this foam thus obtained are as follows:

Density (kg/m$^3$) apparent in free expansion: 24
λ°(mW/m° C.): 20
Temperature of end of degradation of the urethanes (° C.): 300
Loss of weight (%): 21
ΔP %, 400° C. (%): 31

$\frac{\Delta V}{V}$ (%) (after 14 days at 70° C., 95% RH) (%): 3

EXAMPLE 6

The starting polyalcohol is constituted by glycerol (aliphatic polyalcohol of formula $CH_2OH$—$CHOH$—$CH_2OH$) which is reacted with furyloxiran of following formula:

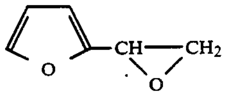

as chain extension agent, with a proportion of furyloxiran of 338% by weight, relatively to the glycerol, for 6 hours at room temperature with 0.5% by weight of KOH as catalyst.

A furan polyol is thus obtained having a hydroxyl index equal to 590, a functionality of 3.

This furan polyol thus obtained is then used for the formulation of polyurethane foam according to the following formulation referenced $F_6$:

Formulation $F_6$:
Furan polyol: 100 parts
Surfactant (Sr242 ® of Schell): 2 parts
Catalyst (DMCHA ® of BASF): 2 parts
$H_2O$: 1 part
Expanding agent (Freon ®): 40 parts
Isocyanate MDI: 112 parts With such a formulation, a cream time of 24 s is obtained and a filament time of 39 s, and the polyurethane foam obtained presents the following characteristics:

Density (kg/m$^3$) apparent in free expansion 27.9
λ°mW/m° C.): 21.0
Temperature of the end of degradation of the urethanes (° C.): 340
Loss of weight (%): 24
ΔP %, 400° C. (%): 35

$\frac{\Delta V}{V}$ (%) (after 7 or 14 days at 70° C., 95% RH) (%): 7 days: 0.4
14 days: 0.8

EXAMPLE 7 WITH AN AMINE

The starting amine is constituted by triethanolamine of following formula:

$(HOH_2C—CH_2l)_3N$

Triethanolamine is a polyhydroxylated amine and therefore also constitutes a polyalcohol which is aminated.

Triethanolamine is reacted with furyloxiran as chain extension agent, the proportion of furyloxiran being of 220% by weight with respect to triethanolamine i.e. 3 molecules of furyloxiran per triethanolamine molecule. The reaction occurs without catalyst and begins at about 50° C. while being exothermic.

The furan polyol thus obtained presents a hydroxyl index of 470 with a functionality of 3.

This furan polyol thus obtained is used for the formulation of polyurethane foam, according to the following formulation referenced $F_7$:

Formulation $F_7$:
Furan polyol hereinabove: 100 parts
Surfactant (Sr242 ® of Schell): 2 parts
Catalyst (DMCHA ® of BASF): 0.5 parts
$H_2O$: 1 part
Expanding agent (Freon ®): 40 parts
Isocyanate MDI: 134 parts
Non-reactive fluidizing agent: 5 parts This formulation gives a cream time of 35 s. and a filament time of 57 s.

The characteristics of the polyurethane foam thus obtained are as follows:

Density (kg/m$^3$) apparent in free extension: 28.8
λ°(mW/m° C.): 21.7
Temperature of the end of degradation of the urethanes (° C.): 320
Loss of weight (%): 31
ΔP %, 400° C. (%): 41

$\frac{\Delta V}{V}$ (%) at 70° C., 95% RH (%): 3 after 28 days.

COMPARATIVE EXAMPLE 8

The polyol used is constituted by the non-furannic aminated polyol marketed by the firm DOW CHEMICAL under reference RA 505, having a hydroxyl index equal to 505, which is a polyol for producing rigid polyurethane foams with excellent performances.

This comparison polyol is used for the formulation of polyurethane foam, in accordance with the following formulation referenced $DF_8$:

Comparison formulation $DF_8$:
Polyol RA 505: 100 parts
Surfactant (Sr242 ® of Schell): 2 parts
Catalyst (DABCO 33LV ® of Air Products): 5 parts
$H_2O$: 2 parts
Expanding agent (Freon ®): 40 parts
Isocyanate MDI: 143 parts The reaction of these components makes it possible to obtain a polyurethane foam presenting a cream time of 11 s and a filament time of 28 s presenting the following characteristics:

Density (kg/m$^3$l) apparent in free expansion: 27.6
λβ(mW/m° C.): 17.2
Temperature of end of degradation of the urethanes (° C.): 350

Loss of weight (%): 51
$\Delta P$ % 400° C.: 60

$$\frac{\Delta V}{V} \text{ (\%) (at 70° C., 95\% RH) (\%): 14 days: 10.1; 1 day: 4.6}$$

COMPARATIVE EXAMPLE 9

The comparison polyol used is a conventional polyol marketed by the firm ICI under the trade name P130 presenting a mean hydroxyl index of 460, also reputed as producing rigid polyurethane foams giving excellent performances.

This polyol is used as such for the formulation of polyurethane foam under the following formulation referenced $CF_9$:

Comparison formulation $CF_9$
Polyol P130 hereinabove: 100 parts
Surfactant (SR242 ® of Schell): 2 parts
Catalyst (DABCO 33LV ® of Air Products): 5 parts
Expanding agent (Freon ®): 40 parts
Isocyanate MDI: 154 parts The reaction of these components makes it possible to produce a polyurethane foam which presents a cream time of 11 s and a filament time of 44 s, having the following characteristics:

Density (kg/m$^3$) apparent in free expansion: 23.1
$\lambda_o$(mW/m° C.): 0.021
Temperature of end of degradation of the urethanes (° C.): 330
Loss of weight (%) 41; $\Delta P$ % 400° C. (%): 52.5

$$\frac{\Delta V}{V} \text{ (\%) (at 70° C., 95\% RH) (\%): 14 days: 10.8; 1 day: 4.9}$$

COMPARATIVE EXAMPLE 10

The comparison example used is a polyol obtained by oxypropylation of 2,5-bis-(hydroxy) furan as set forth in FR-A-2536750 (page 17, Table II, sample 2-B-having a measured hydroxyl index of 515. This polyol is used as such for the formulation of a polyurethane foam under the following formulation referenced $CF_{10}$:

Comparison formulation $CF_{10}$
Polyol 2l-B Table II of FR-A-2536750: 100 parts
Surfactant (Sr242 ® of Schell): 2 parts
Catalyst (DABCO 33LV ® of Air Products): 5 parts
$H_2O$: 2 parts
Expanding agent (Freon ®11): 40 parts
Isocyanate MDI: 162 parts The reaction of these components makes it possible to produce a polyurethane foam which presents a cream time of 17 s and a filament time of 32 s, having the following characteristics:

Density (kg/m$^3$) apparent in free expansion: 25.3
$\lambda_o$(mW/m° C.): 23.0
Temperature of end of degradation of the urethanes (° C.): 330
Loss of weight (%): 37; $\Delta P$ % 400° C. (%): 46

$$\frac{\Delta V}{V} \text{ (\%) (at 70° C., 95\% RH) (\%): 12 days: 20; 20 days: 26.5}$$

It is clearly apparent from the preceding Examples that an unexpected improvement is obtained in the properties of the polyurethanes prepared with the aid of the furan polyols according to the invention.

Comparative Examples 8 to 10 demonstrate this unexpected improvement in the properties obtained with the furan polyols according to the invention.

The polyalcohol or amine used may naturally comprise one or more furan cycles. According to a particular feature, it is used a hydroxylated amine which can be in that case a tertiary amine as previously outlined, (among which a preferred example is triethanolamine).

It will be observed that the polyol produced by the reaction according to the invention may comprise furan cycles in the chain or pendant from this same chain depending on the position and/or the number of the functional groups on the furan cycle.

It should be noted that the use of furan epoxide, particularly a furannic oxiran of formula II abovesaid, is very advantageous as it is highly reactive and avoids the use of a basic catalyst of KOH type which must be neutralized subsequently, as the polyols must not be basic, being given that the basicity reduces the reaction with the isocyanates.

As Example 4 demonstrates, no catalyst being used, it may be observed that, even by carrying out the reaction at ambient temperature, which is a considerable commercial advantage, the duration of the reaction is perfectly acceptable, viz. 48 hrs. In this way, the reaction time is considerably reduced by operating at moderate temperature, for example about 50° C.

Thanks to the dimensional stability under hot, damp conditions, they are of considerable interest for tropical countries and even in Europe for outside use.

It will thus be readily understood that the invention includes all the means constituting technical equivalents, the means described and their various combinations.

The starting strain (polyalcohol or mono- or poly-)amine) may itself be obtained by reaction of a primary or secondary amine (mono- or polyamine) with a chain extension agent preferably formed by an organic epoxide which may be a furan epoxide, as herein defined.

In the event of the strain not being a liquid, it may advantageously be pasted with extended polyol or amine before oxylation is effected.

During chain extension, the temperature is regulated to a fixed value adjustable between ambient temperature and 160° C. depending on the nature of the oxyran and the reactivity of the strain used. A rise in temperature accelerates the speed of reaction without the addition of basic catalyst, such as KOH, from about 0 to 250 ppm.

The durations may thus range from some hours to more than 1 day, as demonstrated in the Examples.

In the description and claims, furan "cycle" is equivalent to furan "ring".

It is also advantageous to use as polyalcohol, the polyalcohols obtained by the process described in EP 0 234 065, preferably the polyalcohols obtained in examples 1 to 3.

What is claimed is:

1. A polyurethane including a polyisocyanurate which is the reaction product of at least one isocyanate with at least one polyol, said polyol comprising at least in part a furan polyol which is the reaction product of:

a) an initiator compound selected from the group consisting of a polyalcohol, a monoamine, a polyamine, and mixtures thereof; and b) an organic epoxide chain extension agent, said initiator compound containing at least one furan moiety other than exclusively 2,5 bis-(hydroxymethyl)furan moieties when said chain extension agent is furan moiety free, and said chain extension agent being a furan-containing epoxide when said initiator compound is furan moiety free.

2. The polyurethane according to claim 1, wherein said polyalcohol is a $C_1$–$C_4$ aliphatic polyalcohol.

3. The polyurethane according to claim 1, wherein said aliphatic polyalcohol is selected from the group consisting of ethylene glycol, propylene glycol, glycerine, trimethylolpropane, pentaerythritol and sorbitol.

4. The polyurethane according to claim 1, wherein said amine or polyamine is primary or secondary and contains at least one hydroxy functionality.

5. The polyurethane according to claim 1, wherein said initiator compound is obtained by the reaction of a mono or polyamine with an epoxide chain extension agent.

6. The polyurethane according to claim 1, wherein said organic epoxide chain extension agent is propylene oxide.

7. The polyurethane according to claim 1, wherein said organic epoxide chain extension agent is a furan-containing epoxide.

8. The polyurethane according to claim 7, wherein said furan-containing epoxide corresponds to the formula:

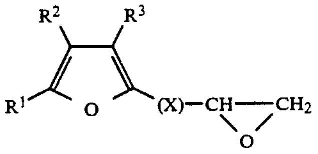

wherein $R^1$, $R^2$, and $R^3$ is H, $C_1$–$C_5$ alkyl group, $C_1$–$C_4$ aliphatic alcohol group, $C_1$–$C_4$ aliphatic acid group, $C_1$–$C_5$ alkyl ester group, $C_1$–$C_4$ aliphatic ketone group, $C_1$–$C_4$ aliphatic aldehyde group or mixtures thereof and (X) is an organic radical.

9. The polyurethano according to claim 8, wherein said organic radical is a $C^1$–$C^{10}$ aliphatic radical.

10. A polyurethane including a polyisocyanurate which is the reaction product of at least one isocyanate with at least one polyol, said polyol comprising at least in part a furan polyol which is the reaction product of:

a) a polyalcohol initiator compound, b) a furan containing epoxide chain extension agent, thereby having pending furan moieties in the furan polyol reaction product.

11. A polyurethane including a polyisocyanurate which is the reaction product of at least one isocyanate with at least one polyol, said polyol comprising at least in part a furan polyol which is the reaction product of:

a) an initiator compound comprising a polyalcohol; and b) an organic epoxide chain extension agent, said polyalcohol corresponding to the formula:

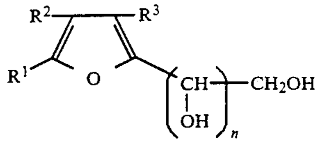

wherein $R^1$, $R^2$, and $R^3$ is H, $C_1$–$C_5$ alkyl group, $C_1$–$C_4$ aliphatic alcohol group, $C_1$–$C_4$ aliphatic acid group, $C_1$–$C_5$ alkyl ester group, $C_1$–$C_4$ aliphatic ketone group, $C_1$–$C_4$ aliphatic aldehyde group or mixtures thereof; $n=0$ to 10, provided that when $n=0$, at least one of the $R^1$, $R^2$, $R^3$ is a group with alcohol function, $R^1$ not being able to be $CH_2OH$ if the chain extension agent does not contain a furan cycle.

12. The polyurethane according to claim 11, wherein n is 1 to 10.

13. The polyurethane according to claim 12, wherein n is 1 to 3.

14. The polyurethane according to claim 11, wherein $R^1$ is H, $CH_3$ or $CH_2OH$ and when $R^1$ is $CH^2OH$, $n=1$ to 10, $R^2$ is H, a $C_1$–$C_5$ alkyl group, $C_1$–$C_4$aliphatic alcohol group, $C_1$–$C_4$ aliphatic acid group, $C_1$–$C_5$ alkyl ester group, $C_1$–$C_4$ aliphatic ketone group $C_1$–$C_4$ aliphatic aldehyde group or mixtures thereof; and $R^1$ is H or a $C^1$–$C^5$ alkyl group.

15. The polyurethane according to claim 14, wherein $R^3$ is a $C_1$–$C_3$ alkyl group.

16. The polyurethane according to claim 15, wherein $R^3$ is $CH_3$ or $C_2H_5$.

17. The polyurethane according to claim 11, wherein said polyalcohol corresponds to the formula:

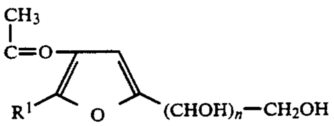

wherein n is 1 to 10.

18. The polyurethane according to claim 11, wherein said organic epoxide chain extension agent is a furan-containing epoxide.

19. The polyurethane according to claim 18, wherein said furan-containing epoxide corresponds to the formula:

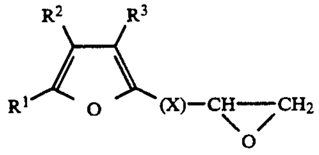

wherein $R^1$, $R^2$, and $R^3$ is H, $C_1$–$C_5$ alkyl group, $C_1$–$C_4$ aliphatic alcohol group, $C_1$–$C_4$ aliphatic acid group, $C_1$–$C_5$ alkyl ester group, $C_1$–$C_4$ aliphatic ketone group, $C_1$–$C_4$ aliphatic aldehyde group or mixtures thereof and (X) is an organic radical.

20. The polyurethane according to claim 11, wherein said organic epoxide chain extension agent is propylene oxide.

21. A polyurethane including a polyisocyanurate which is the reaction product of at least one isocyanate with at least one polyol, said polyol comprising at least in part a furan polyol which is the reaction product of:

a) an initiator compound comprising a monoamine or a polyamine; and b) an organic epoxide chain extension agent, said initiator containing at least one pending furan moiety when said chain extension agent is furan moiety free and said chain extension agent being a furan containing epoxide when said initiator is furan moiety free, thereby having pending furan moieties in the furan polyol.

22. The polyurethane according to claim 21, wherein said organic epoxide chain extension agent is propylene oxide.

23. The polyurethane according to claim 21, wherein said organic epoxide chain extension agent is a furan-containing epoxide.

24. The polyurethane according to claim 23, wherein said furan-containing epoxide corresponds to the formula:

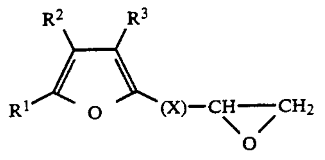

wherein $R^1$, $R^2$, and $R^3$ is H, $C_1$–$C_5$ alkyl group, $C_1$–$C_4$ aliphatic alcohol group, $C_1$–$C_4$ aliphatic acid group, $C_1$–$C_5$ alkyl ester group, $C_1$–$C_4$ aliphatic ketone group, $C_1$–$C_4$ aliphatic aldehyde group or mixtures thereof and (X) is an organic radical.

25. The polyurethane according to claim 24, wherein said organic radical is a $C^1$–$C^{10}$ aliphatic radical.

26. A polyurethane including a polyisocyanurate which is the reaction product of at least one isocyanate with at least one polyol, said polyol comprising at least in part a furan polyol which is the reaction product of:

a) an initiator compound selected from the group consisting of a primary monoamine, a primary polyamine, a secondary monoamine, a secondary polyamine, a hydroxylated tertiaryamine containing at least two hydroxy functions, b) a furan-containing organic epoxide chain extension agent thereby having pending furan moieties in the furan polyol reaction product.

27. A polyurethane including a polyisocyanurate which is the reaction product of at least one isocyanate with at least one polyol, said polyol comprising at least in part a furan polyol which is the reaction product of:

a) an initiator compound comprising an aminated polyalcohol obtained by reacting an amine other than a tertiary amine with a furan-containing epoxide, and b) an organic epoxide chain extension agent, thereby having pending furan moieties in the furan polyol reaction product.

28. A polyurethane including a polyisocyanurate which is the reaction product of at least one isocyanate with at least one polyol, said polyol comprising at least in part a furan polyol which is the reaction product of:

a) an initiator compound comprising an amine selected from the group consisting of $NH_3$, methylamine, methylenediamine, ethylamine, ethylenediamine, propylamine, 1,3-propyldiamine, EDTA, and triethanolamine, and b) a furan-containing epoxy compound thereby having pending furan moieties in the furan polyol.

29. A polyurethane including a polyisocyanurate which is the reaction product of at least one isocyanate with at least one polyol, said polyol comprising at least in part a furan polyol which is the reaction product of:

a) an initiator compound comprising a polyalcohol corresponding to the formula:

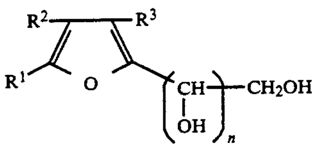

wherein $R^1$, $R^2$, and $R^3$ is H, $C_1$–$C_5$ alkyl group, $C_1$–$C_4$ aliphatic alcohol group, $C_1$–$C_4$ aliphatic acid group, $C_1$–$C_5$ alkyl ester group, $C_1$–$C_4$ aliphatic ketone group, $C_1$–$C_4$ aliphatic aldehyde group or mixtures thereof; $n=1$ to 10; and b) an organic epoxide chain extension agent, thereby having pending furan moieties in the furan polyol reaction product.

30. The polyurethane according to claim 29, wherein n is 1 to 3.

31. The polyurethane according to claim 29, wherein $R^1$ is H, $CH_3$ or $CH_2OH$, $R^2$ is H, a $C_1$–$C_5$ alkyl group, $C_1$–$C_4$aliphatic alcohol group, $C_1$–$C_4$ aliphatic acid group, $C_1$–$C_5$ alkyl ester group, $C_1$–$C_4$ aliphatic ketone group $C_1$–$C_4$ aliphatic aldehyde groupe or mixtures thereof; and R is H or a $C^1$–$C^5$ alkyl group.

32. The polyurethane according to claim 31, wherein $R^3$ is a $C_1$–$C_3$ alkyl group.

33. The polyurethane according to claim 32, wherein $R^3$ is $CH_3$ or $C_2H_5$.

34. A polyurethane including a polyisocyanurate which is the reaction product of at least one isocyanate with at least one polyol, said polyol comprising at least in part a furan polyol which is the reaction product of:

a) an initiator compound comprising a polyalcohol of formula:

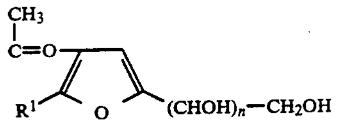

wherein n is 1 to 10, and b) an organic epoxide chain extension agent thereby having pending furan moieties in the furan reaction product.

35. The polyurethane according to claim 29, wherein said organic epoxide chain extension agent is a furan-containing epoxide.

36. The polyurethane according to claim 35, wherein said furan-containing epoxide corresponds to the formula:

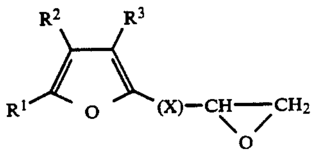

wherein $R^1$, $R^2$, and $R^3$ is H, $C_1$–$C_5$ alkyl group, $C_1$–$C_4$ aliphatic alcohol group, $C_1$–$C_4$ aliphatic acid group, $C_1$–$C_5$ alkyl ester group, $C_1$–$C_4$ aliphatic ketone group, $C_1$–$C_4$ aliphatic aldehyde group or mixtures thereof and (X) is an organic radical.

37. The polyurethane according to claim 29, wherein said organic epoxide chain extension agent is propylene oxide.

38. A polyurethane including a polyisocyanurate which is the reaction product of at least one isocyanate with at least one polyol, said polyol comprising at least in part a furan polyol which is the reaction product of:

a) an initiator compound selected from the group consisting of a polyalcohol, a monoamine, a polyamine, and mixtures thereof; and b) an organic epoxide chain extension agent, said epoxide chain extension agent being a furan-containing epoxide, thereby having pending furan moieties in the furan polyol reaction product.

39. The polyurethane according to claim 38, wherein said polyalcohol is a $C_1$–$C_4$ aliphatic polyalcohol.

40. The polyurethane according to claim 39, wherein said aliphatic polyalcohol is selected from the group consisting of ethylene glycol, propylene glycol, glycerine, trimethylolpropane, pentaerythritol and sorbitol.

41. The polyurethane according to claim 38, wherein said amine or polyamine is primary or secondary and contains at least one hydroxy functionality.

42. The polyurethane according to claim 38, wherein said initiator compound is obtained by the reaction of a mono or polyamine with an epoxide chain extension agent.

43. The polyurethane according to claim 38, wherein said furan-containing epoxide corresponds to the formula:

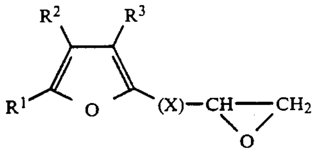

wherein $R^1$, $R^2$, and $R^3$ is H, $C_1$–$C_5$ alkyl group, $C_1$–$C_4$ aliphatic alcohol group, $C_1$–$C_4$ aliphatic acid group, $C_1$–$C_5$ alkyl ester group, $C_1$–$C_4$ aliphatic ketone group, $C_1$–$C_4$ aliphatic aldehyde group or mixtures thereof and (X) is an organic radical.

44. The polyurethane according to claim 43, wherein said organic radical is a $C^1$–$C^{10}$ aliphatic radical.

45. A polyurethane including a polyisocyanurate which is the reaction product of at least one isocyanate with at least one polyol, said polyol comprising at least in part a furan polyol which is the reaction product of:

a) an initiator compound comprising a tertiaryamine being the reaction product of a furan free amine and furannic oxiran, and b) an organic epoxide chain extension agent, thereby having pending furan moieties in the furan polyol.

46. The polyurethane according to claim 45, wherein said organic epoxide chain extension agent is propylene oxide.

47. The polyurethane according to claim 45, wherein said organic epoxide chain extension agent is a furan-containing epoxide.

48. The polyurethane according to claim 47, wherein said furan-containing epoxide corresponds to the formula:

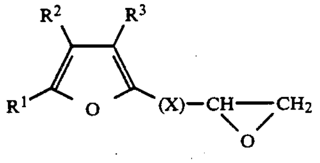

wherein $R^1$, $R^2$, and $R^3$ is H, $C_1$–$C_5$ alkyl group, $C_1$–$C_4$ aliphatic alcohol group, $C_1$–$C_4$ aliphatic acid group, $C_1$–$C_5$ alkyl ester group, $C_1$–$C_4$ aliphatic ketone group, $C_1$–$C_4$ aliphatic aldehyde group or mixtures thereof and (X) is an organic radical.

49. The polyurethane according to claim 48, wherein said organic radical is a $C^1$–$C_{10}$ aliphatic radical.

* * * * *

UNITED STATES PATENT AND TRADEMARK OFFICE
CERTIFICATE OF CORRECTION

PATENT NO. : 5,091,495

DATED : February 25, 1992

INVENTOR(S) : Gabriel Roux, et al

It is certified that error appears in the above-identified patent and that said Letters Patent is hereby corrected as shown below:

In column 12, lines 36-42 and in column 14, lines 45-50, that portion of the formula reading

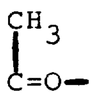 should read 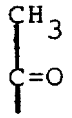

Signed and Sealed this

Thirty-first Day of August, 1993

Attest:

BRUCE LEHMAN

*Attesting Officer* *Commissioner of Patents and Trademarks*